(12) United States Patent
Haq

(10) Patent No.: US 7,412,396 B1
(45) Date of Patent: Aug. 12, 2008

(54) VIRTUAL CLINIC FOR MEDICAL PRACTICE

(76) Inventor: Mohamed M. Haq, 207 Stanley Ct., Galveston County, Friendswood, TX (US) 77546-4544

( * ) Notice: Subject to any disclaimer, the term of this patent is extended or adjusted under 35 U.S.C. 154(b) by 1182 days.

(21) Appl. No.: 09/918,413

(22) Filed: Jul. 30, 2001

Related U.S. Application Data

(60) Provisional application No. 60/269,051, filed on Feb. 15, 2001.

(51) Int. Cl.
G06Q 50/00 (2006.01)

(52) U.S. Cl. .............................. 705/2; 705/3; 600/300

(58) Field of Classification Search ............... 705/2–3; 600/300
See application file for complete search history.

(56) References Cited

U.S. PATENT DOCUMENTS

| | | | |
|---|---|---|---|
| 5,301,105 A * | 4/1994 | Cummings, Jr. ............... | 705/2 |
| 5,307,263 A * | 4/1994 | Brown ........................ | 600/301 |
| 5,339,821 A * | 8/1994 | Fujimoto .................... | 600/513 |
| 5,366,896 A | 11/1994 | Margrey et al. | |
| 5,410,471 A | 4/1995 | Alyfuku et al. | |
| 5,441,047 A * | 8/1995 | David et al. ................. | 600/483 |
| 5,544,649 A | 8/1996 | David et al. | |
| 5,558,638 A | 9/1996 | Evers et al. | |
| 5,576,952 A | 11/1996 | Stutman et al. | |
| 5,715,823 A | 2/1998 | Wood et al. | |
| 5,772,585 A | 6/1998 | Lavin et al. | |
| 5,815,392 A | 9/1998 | Bennett et al. | |
| 5,822,544 A | 10/1998 | Chaco et al. | |
| 5,842,173 A | 11/1998 | Strum et al. | |
| 5,862,223 A | 1/1999 | Walker et al. | |
| 5,867,821 A * | 2/1999 | Ballantyne et al. ............. | 705/2 |
| 5,875,431 A | 2/1999 | Heckman et al. | |
| 5,897,498 A | 4/1999 | Canfield, II et al. | |
| 5,899,855 A | 5/1999 | Brown | |
| 5,911,687 A * | 6/1999 | Sato et al. ................... | 600/300 |
| 5,940,800 A | 8/1999 | Bennett et al. | |
| 5,961,446 A | 10/1999 | Beller et al. | |
| 5,991,733 A | 11/1999 | Aleia et al. | |
| 5,995,939 A | 11/1999 | Berman et al. | |
| 5,997,476 A | 12/1999 | Brown | |

(Continued)

OTHER PUBLICATIONS

Taylor, Kathryn S. "Healthcare and The World Wide Web" May/Jun. 1997. Healthcare Executive. vol. 12, Iss. 3. p. 12.*

(Continued)

*Primary Examiner*—C Luke Gilligan
*Assistant Examiner*—Tran N. Nguyen
(74) *Attorney, Agent, or Firm*—Sheppard Mullin Richter & Hampton LLP

(57) ABSTRACT

A method is provided for a virtual clinic to establish communications and working relationships among itself, patients, physicians, and insurance companies patient to facilitate the remote diagnosis and treatment of patients. In one embodiment, a patient may contact its insurance carrier via a web page on the Internet. The insurance company then matches the patient to one of its plans and then forwards information to the virtual clinic which then responds to the patient's web request. The patient is then put in operative communication with a physician who is known by the virtual clinic to be licensed to practice medicine in the patient's current location and to have expertise in the patient's condition.

40 Claims, 6 Drawing Sheets

U.S. PATENT DOCUMENTS

| | | | |
|---|---|---|---|
| 6,012,035 A * | 1/2000 | Freeman et al. .................. 705/2 |
| 6,014,631 A | 1/2000 | Teagarden et al. |
| 6,018,713 A | 1/2000 | Coli et al. |
| 6,024,699 A * | 2/2000 | Surwit et al. ................. 600/300 |
| 6,050,940 A | 4/2000 | Braun et al. |
| 6,055,506 A | 4/2000 | Frasca, Jr. |
| 6,074,616 A | 6/2000 | Buechler et al. |
| 6,076,066 A | 6/2000 | DiRienzo et al. |
| 6,080,106 A | 6/2000 | Lloyd et al. |
| 6,081,786 A | 6/2000 | Barry et al. |
| 6,083,248 A | 7/2000 | Thompson |
| 6,088,731 A | 7/2000 | Kiraly et al. |
| 6,101,478 A * | 8/2000 | Brown ........................... 705/2 |
| 6,112,224 A | 8/2000 | Peifer et al. |
| 6,113,540 A | 9/2000 | Iliff |
| 6,139,494 A | 10/2000 | Cairnes |
| 6,151,586 A | 11/2000 | Brown |
| 6,159,147 A | 12/2000 | Lichter et al. |
| 6,161,095 A | 12/2000 | Brown |
| 6,168,563 B1 | 1/2001 | Brown |
| 6,171,237 B1 | 1/2001 | Avitall et al. |
| 6,176,826 B1 | 1/2001 | Shimura et al. |
| 6,283,761 B1 * | 9/2001 | Joao ........................... 434/236 |
| 6,403,897 B1 * | 6/2002 | Bluth et al. .................. 177/144 |
| 6,539,101 B1 * | 3/2003 | Black ........................... 382/124 |
| 6,757,898 B1 * | 6/2004 | Ilsen et al. .................. 709/203 |
| 6,957,218 B1 * | 10/2005 | Wyatt .......................... 707/10 |
| 2001/0039504 A1 * | 11/2001 | Linberg et al. ................. 705/3 |
| 2002/0049684 A1 * | 4/2002 | Nagamoto et al. ............. 706/1 |
| 2002/0111831 A1 * | 8/2002 | Harada ......................... 705/3 |
| 2004/0015132 A1 * | 1/2004 | Brown ......................... 604/131 |
| 2004/0019503 A1 * | 1/2004 | Berenguer ...................... 705/2 |
| 2004/0172305 A1 * | 9/2004 | Soerensen et al. .............. 705/3 |
| 2004/0215491 A1 * | 10/2004 | Clark et al. .................... 705/2 |

OTHER PUBLICATIONS

Priest, Lisa. "MDs Cited For Fraud Some 100 Probed Over Kickbacks and Referral Fees" Feb. 26, 1996. Toronto Star. p. A.1.*

Crompton, Simon. "Virtual Hospital Speeds Recovery" Jun. 5, 2001. The Times. p. Times.2.*

SoRelle, Ruth. "Doctor's Referral Fee Is Ruled A Violation" Aug. 1, 1987. Houston Chronicle. p. 18.*

Smith Anderson, Laurie. "Providing Care: Virtual Free Clinic Provides Care In Nine Area Parishes" Sep. 22, 2000. Advocate p. 1.C.*

PR Newswire. Best Doctors, Inc. Launches Internet "Virtual Clinic" Jun. 21, 2000. p. 1.*

Smith Anderson, Laurie. "Providing Care: Virtual Free Clinic Provides Care In Nine Parishes" Sep. 22, 2000. Advocate p. 1.C.*

Crompton, Simon. "Virtual Hospital Speeds Recovery" Jun. 5, 2001. The Times. p. 2.*

* cited by examiner

VIRTUAL CLINIC FOR MEDICAL PRACTICE

CROSS-REFERENCE TO RELATED APPLICATION

This patent application is a conversion of, and claims priority to, commonly owned U.S. Provisional patent application No. 60/269,051, filed Feb. 15, 2001, entitled "Electronic Business Entity for Medical Practice" by Mohamed M. Haq.

BACKGROUND

1. Filed of the Invention

The present invention relates generally to a method for a patient to contact a physician remotely and to receive medical services via a virtual clinic which contracts with doctors and insurance companies, and allows for the patient to submit remotely diagnostic information from his/her home so that a physician may make a diagnosis and recommend treatment.

2. Background of the Related Technology

In the United States alone, nearly a million people visit their doctor at least once (National Center for Health Statistics-http: www.cdc.gov/ncds/fastats/docvisit.htm). The average patient visits a doctor 3.1 times per year. The most frequent principal reason for the visit is a general medical examination, the most frequent diagnostic procedure performed is a blood pressure check, and the most frequent principal diagnosis is upper respiratory tract infection. Other diagnoses in the top 20 categories for which patients visit their doctor include diabetes, arthritis, asthma/bronchitis, sinus infection, etc.

A typical visit to the doctor's office involves the patient completing a questionnaire detailing demographics, insurance/financial or payment procedure, personal information (habits like smoking, occupation), past medical problems, family history, and the reason for the present visit. The physician or one of his/her staff asks the patient additional questions and records the patient's pulse, blood pressure and weight. The physician performs a visual examination of the patient, and may inspect the ears and throat, listen to their heart, lungs and abdomen with a stethoscope, feel the patient's body for enlargement of organs, accumulation of fluid in the body cavities, any lumps or tender spots, range of movements or restriction of various joints and a neurological exam, etc. The physician may then order laboratory investigations such as blood tests, EKG, X-rays, etc. Based on part or all of this database, the physician formulates a diagnosis and, if necessary, recommends a treatment which can be one or all of the following:

1. Medicines
2. Surgery
3. Physical therapy
4. Rest
5. Observation
6. Additional evaluation, consultations, diagnostic testing, etc.

Follow up visits for minor complaints such as a sore throat usually do not require thorough examination. Follow-up visits to reassess the effectiveness of blood pressure medicines or diabetic medicines typically involve a discussion and/or limited examination. Doctors usually maintain offices in expensive medical buildings, have staffs which command high salaries, have multiple phone lines and other overhead expenses which are ultimately all added to the patients' bills.

The patient or his or her legal guardian typically makes an appointment to see the doctor days to weeks in advance, mostly at the doctor's convenience, leaves the home or office, drives several miles, misses work, tries to find a parking spot (which may not be available or gratis), and waits in the doctor's office before he or she is seen.

Most of the office visits, especially for follow up or for minor complaints, are very brief examinations with the physician, require an inordinate amount of time, and money is wasted in the process. Additionally, the driving back and forth and waiting may exacerbate the patient's condition.

Telemedicine is the use of electronic information and communication technology to provide and support health care when distance separates the participants.

A major drawback of the presently available telemedicine system is its set up cost, which are approximately $100,000 per site. At a minimum, there must be two sites, one for the patient and one for the doctor. Moreover, both the patient and the doctor have to travel to their respective telemedicine facility because the communication signals only begin and/or end at the facility and nowhere else. Furthermore, there are no mechanisms for integrating telemedicine into an existing physician practice to facilitate payment for telemedicine-based services.

There is, therefore, a need in the art for a mechanism which allows for a patient to contact a physician remotely and to receive medical services, wherein the arrangement of services between doctors and insurance companies is facilitated electronically and provides the ability for patients to submit diagnostic testing to a physician and to correspond with that physician, such that they can receive a diagnosis and treatment.

SUMMARY OF THE INVENTION

The present invention is a system and method for enabling patients, with equipment readily available off the shelf, to correspond in real-time with their physicians without the need for expensive facilities in remote locations. The present invention simplifies the material requirements by utilizing, for example, a personal computer (PC) equipped with a digital camera. Patients can use standard diagnostic equipment, such as a thermometer, stethoscope, etc. that are often kept at the home. The PC can be equipped with Internet connectivity and a web browser that can render web pages provided by a virtual clinic that establishes the connection between the patient and the doctor. The particular doctor is chosen by the virtual clinic based upon a variety of factors, including, but not limited to, time of day, availability of the patient's standard physician, type of medical condition, etc. The virtual clinic then provides the proper connectivity between the selected physician and the patient or otherwise enables them to communicate. The doctor can then instruct the patient to perform the necessary measurements and, through textual, image, audio and/or visual means, diagnose the problem and recommend appropriate treatment.

An exemplary embodiment of the present invention is directed to a method and system for establishing a virtual clinic. Specifically, a virtual clinic is created by establishing communications and working relationships with patients, physicians, and insurance companies to facilitate the remote diagnosis and treatment of patients. In the first exemplary embodiment, a patient may contact his/her insurance carrier via a web page on the Internet. The insurance company then matches the patient to one of its plans and then forwards information to the virtual clinic, which then responds to the patient's web request. The patient is then put in operative communication with a physician that is known by the virtual clinic to be licensed to practice medicine in the patient's current location and to have expertise in the patient's condition.

Another exemplary embodiment of the invention is directed to a method for a patient to contact remotely a physician and to receive medical services from that physician. The method includes the steps of: the patient contacting a virtual clinic via a wide area network such as the Internet; the patient providing information on his or her medical condition; the virtual clinic identifying automatically a physician based on the patient provided medical condition information; the patient corresponding with the physician; the patient submitting diagnostic testing to the physician; and the physician informing the patient of the treatment.

The present invention provides a method and system to diagnose and treat certain ailments without the patient ever leaving his/her home or place of work and without the doctor needing an office. The present invention thus provides tremendous savings for the patient (precluding the need for driving and loss of time at work, etc.) and for the doctor (precluding the need for an expensive office), in addition to the convenience and increase in productivity.

The invention relates to a virtual clinic, which allows remotely located physicians (or other professionals) to perform medical examinations and consultations with remotely located patients (or clients). Patients access the physicians (and vice-versa) using the virtual clinic which allows the parties to interact via a wide area communication network such as the Internet, or other electronic, satellite, or digital media, or other type of remote consumer business-to-business communication system. The virtual clinic can provide secured access, pre-established contracts to perform professional services, appointments, referrals, and any other information or service to facilitate interaction between patients and physicians. The virtual clinic provides for the input, storage, manipulation, and retrieval of patients' medical records or data, and can also store notes from the physician for future reference by the same or a different physician. The virtual clinic may also provide medical and electronic equipment at remote sites for access and use by patients or others. The equipment may include computers (with access to a communication network), a camera or other means of recording and/or transmitting images, and medical equipment, such as thermometer, stethoscope, ultrasound machines, EKG machines, and other medical equipment. All equipment may have the capability to input and transmit data to the virtual clinic for storage, manipulation, access, or retrieval of the data by others. The present invention is equally applicable to other professionals, such as attorneys, accountants, etc.

Features and advantages of the invention will be apparent from the following description of the embodiments, given for the purpose of disclosure and taken in conjunction with the accompanying drawings.

BRIEF DESCRIPTION OF THE DRAWINGS

A more complete understanding of the present disclosure and advantages thereof may be acquired by referring to the following description taken in conjunction with the accompanying drawings, wherein.

Figure 1:
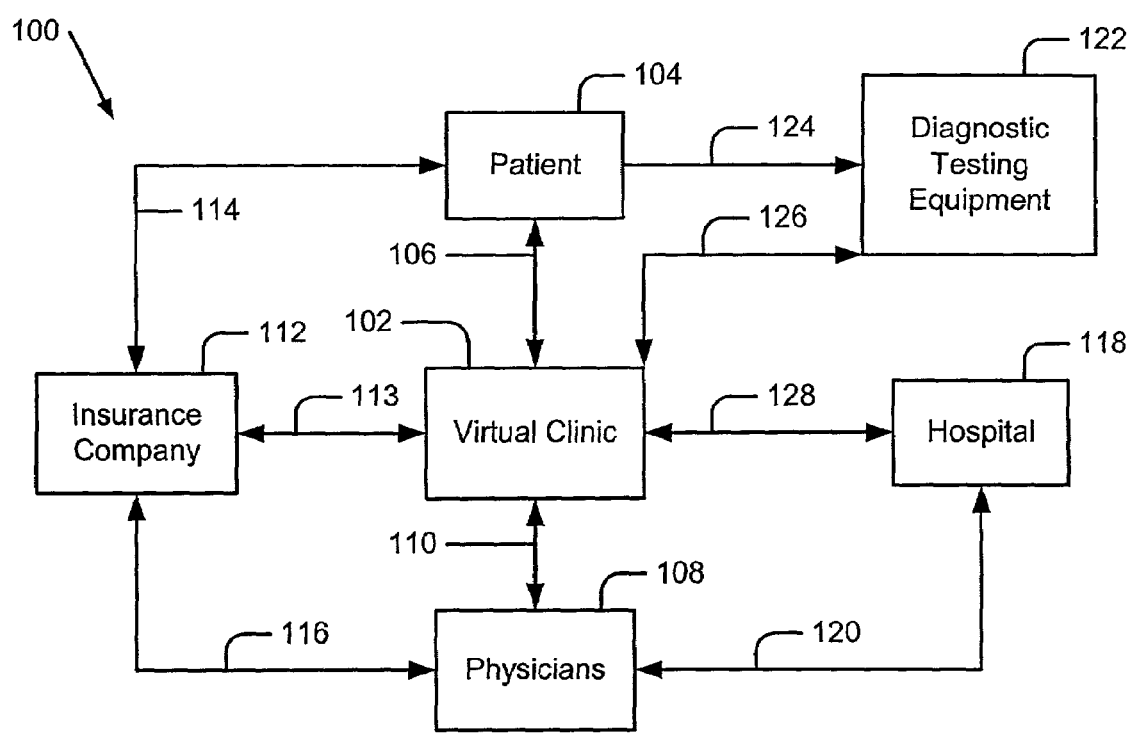
FIG. 1 is a schematic representation of the present invention showing the relationships between the virtual clinic and other entities.

While the present invention is amenable to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

The present invention is directed to a method for a patient to remotely contact a physician and receive medical services which utilizes a virtual clinic to contract with physicians and insurance companies and which facilitates the identification of, and contact with, a physician, based upon the patient's medical condition. The present invention enables the patient to submit to diagnostic testing and forwards the results to the physician who can then correspond directly with the patient.

As used herein, a "virtual clinic" is a professional association such as a corporation or partnership having a presence in a telecommunications media, such as, the Internet, that hires or otherwise contracts with physicians and/or insurance companies and provides services somewhat comparable to clinics or hospitals. The virtual clinic can be a hardware device that is connected to a suitable network, or a software program running on a computer system that is connected to the network, or any combination there between. The virtual clinic can be run autonomously, or it can have one or more human operators. Ideally, the virtual clinic is provided with circuitry and/or logic that enables the clinic to receive information from a patient and/or the patient's insurance carrier or employer in order to determine which of the physicians, nurses, nurses' assistants, physicians' assistants, or other medical personnel would be best able to handle the patient's request within legal limits.

Before the virtual clinic receives requests from patients, it first establishes contracts or other working relationships with one or more physicians and other medical personnel. Information, such as licensures, specialization, experience, hospital affiliations, etc. are stored by the virtual clinic and are used to match a patient's needs to the available medical personnel who are affiliated with the virtual clinic. Additional contracts or working relationships can be established between insurance carriers and/or employers in order to provide benefits to their insured or employees, respectively.

Once the virtual clinic establishes sufficient working relationships with physicians and/or insurance carriers and/or employers, it creates a presence on the network by, for example, creating a web page that enables a patient to request consultation with a medical professional. Similarly, an arrangement with an employer or insurance company can be established so that when a patient views his/her carrier's or employer's web site, the patient is forwarded to the virtual clinic's web site. Sufficient information can be transmitted during the forwarding process to identify either (or both) the insurance carrier/employer and the patient in order for the virtual clinic's response to be tailored as desired. Such tailoring can include the use of trademarks or style that is similar to the styling or trade dress of the first site visited by the patient. This is a useful technique to give the patient the impression that they are communicating with the correct (approved) web site.

Once the patient communicates his/her identifying information and medical complaint/condition, a human and/or machine associated with the virtual clinic can interpret the request and determine which medical professional should be consulted based on an appropriate set of criteria that can include, but is not limited to, the patient's current location (for legal licensure constraints), condition (for specialization), and time (availability of the medical professional within a time zone having those working hours). Once selected, the virtual clinic establishes communications with the medical professional (typically a physician) and then either coordinates the communications link between the physicians and patient or simply tells the patient or physician how to contact the other party directly.

The virtual clinic can do more than simply facilitate communications. The virtual clinic can also store and retrieve patient information by a medical professional, insurance carrier or employer. Moreover, the virtual clinic can also facilitate the payment of fees and expenses incurred by the medical professionals in the course of caring for the patient. For example, after the medical professional and patient have concluded their visit, the physician can submit a bill to the virtual clinic which will then handle the bill on the physician's behalf with either the insurance carrier, the employer, or the patient.

In a first preferred embodiment, a virtual clinic establishes contracts or other working arrangements with physicians and patients (or patient's employers or patient's insurance company) to provide the service. The virtual clinic also establishes communication links between itself and the patients and physicians, typically through a wide area network such as the Internet. For example, patients can utilize their PC's at their home or at work to log on the web site of the business. An appointment time is given or the patient may request urgent care. The patient will sign electronically a consent to receive medical treatment and a contract to pay for the services. The virtual clinic can charge the patient's insurance company, or charge the patient directly for the service and reimburse the doctor for the doctor's portion. Alternatively, the insurance company may have an existing contract with the doctor in which case the insurance company will pay the virtual clinic for its portion of the service and handle the doctor's fees per the contract. In yet another embodiment, the doctor bills the patient directly and the doctor pays a fee to the virtual clinic as a service provider.

The virtual clinic advertises its services, provides a list of supplies needed at home or at the PC which the patient utilizes to be evaluated by the doctor (see list of "preferred equipment" below). It provides instructions on-line to the patient on the use of the various equipment and supplies. It provides the hardware and software necessary for patients to access them and be connected to the physicians.

The physician utilizes a PC, preferably with a computer camera or digital video camera and access to the Internet. He or she signs a contract with the virtual clinic to provide telemedicine services. He or she agrees to be available at specific hours or at any hour. He or she agrees to evaluate patients only by appointment or be available for patients needing urgent care without appointment. He or she may agree to evaluate only established patients or to accept new patients. The physician may be licensed to practice in one or more states, but would be limited to practice only in the state(s) in which he/she is licensed.

The virtual clinic maintains a list of the physicians with their specialities, their qualifications and relevant information (board certification, school and year of graduation, experience and expertise, etc.).

When a patient accesses the virtual clinic, he/she is asked to choose a physician from among those on their panel, or if the patient does not have a preference or needs urgent care and his/her personal choice is not available for providing urgent care, the virtual clinic connects him/her to an appropriate physician in the specialty which the patient is seeking.

Referring now to the drawings, the details of an exemplary embodiment of the present invention is schematically illustrated. FIG. 1 depicts an example of the relationships that the virtual clinic 102 has with other entities. The virtual clinic 102 serves patients 104 in a number of relationships 106. For example, the patient 104 supplies information about his medical condition to the virtual clinic 102 and the virtual clinic 102 selects an appropriate physician 108 who provides a diagnosis and treatment back to the patient 104 through the virtual clinic 102 through relationship 106.

The virtual clinic 102 also has a number of relationships 110 with physicians 108, for example, the virtual clinic 102 refers patients 104 to the physicians 108 through relationship 110.

The virtual clinic 102 also has relationships 113 with insurance companies 112, such as insurance companies 112 reimbursing the virtual clinic 102 for medical services arranged by the virtual clinic 102.

The patients 104 may have existing relationships 114 with insurance companies 112, such as a group insurance policy. Physicians 108 may also have relationships 116 with insurance companies 112, such as physicians 108 providing discounted medical services upon referrals by insurance companies 112. Physicians 108 may also have relationships 120 with hospitals 118, such as privileges at certain hospitals 118.

The virtual clinic 102 may have relationships 128 with at least one hospital 118, for example, the virtual clinic 102 may contract with one or more hospitals to provide diagnostic testing to the virtual clinic or to provide medical services which require the patient's presence (e.g., stitches, setting broken bones, etc.).

The present invention is useful with equipment that is readily available off-the-shelf. For example, a personal computer (PC) equipped with a digital camera can be used to transmit images from the patient to the doctor. Patients can use standard diagnostic equipment, such as a thermometer, stethoscope, etc. that are often kept at the home. It is preferred, however, that the patient have at their home a digital thermometer and digital stethoscope that can input real-time data into a PC for immediate use by the physician or other medial professional. The PC or other communication device can, for example, be equipped with Internet connectivity and a web browser that can render web pages that are provided by the virtual clinic. Based upon information uploaded by the patient, as well as an optional comparison with patient information retrieved from a database, the time of day, the availability of the patient's standard physician, the type of medical condition, etc., a particular doctor is selected by the virtual clinic. The virtual clinic then provides the proper connectivity between the selected physician and the patient or otherwise enables them to communicate. The doctor can then instruct the patient to perform the necessary measurements and, through textual, image, audio and/or visual means, diagnose the problem and recommend appropriate treatment.

While the present invention can work with the equipment mentioned above, it is envisioned that some patients with chronic conditions such as diabetes, will have purchased additional equipment not found in most households. This diagnostic testing equipment can itself contain telecommunications/Internet connectivity to facilitate the uploading of test results to the physician via the communications link established by the virtual clinic. Preferably, diagnostic testing equipment 122 is in communication 126 with the virtual clinic 102, such that patients 104 can access 124 the diagnostic testing equipment 122 and submit the diagnostic testing results to the virtual clinic 102 through communication 126 and ultimately to physicians 108.

Figure 2:
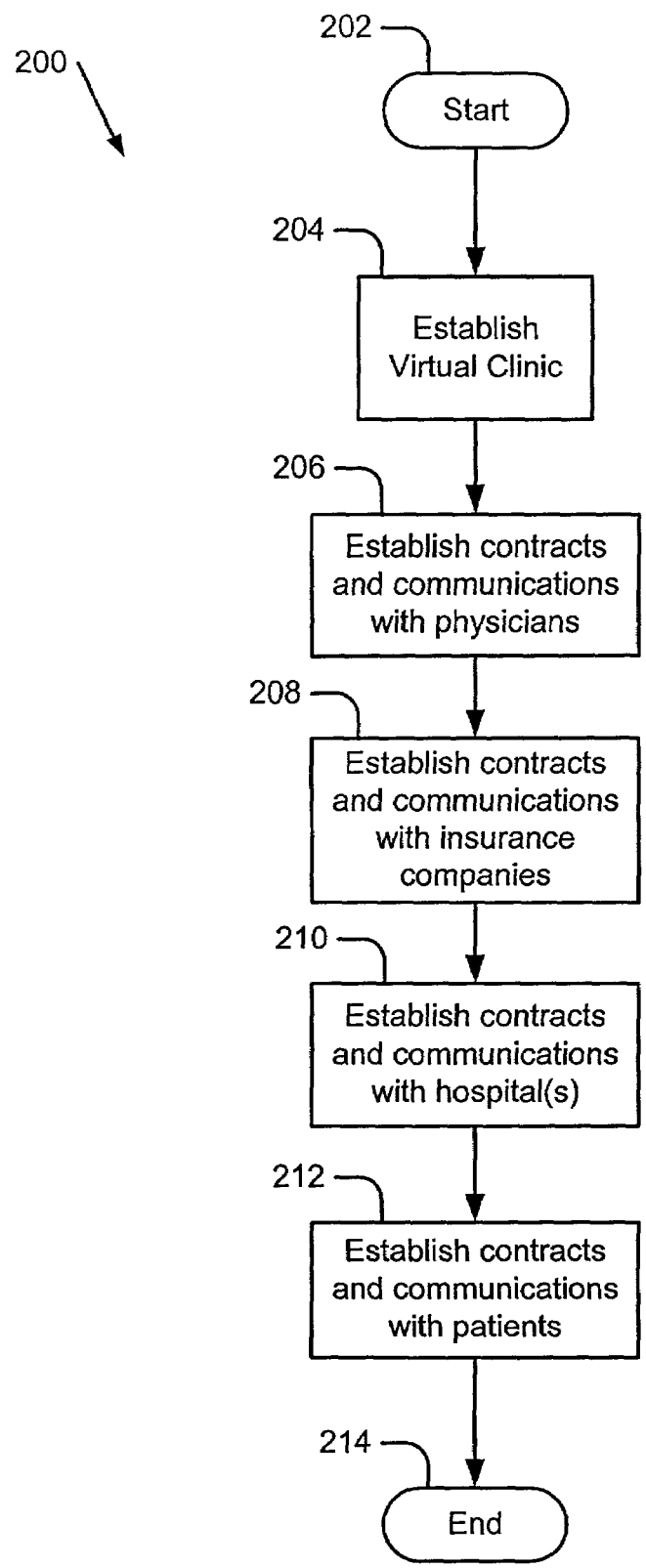
FIG. 2 is a schematic representation showing the establishment of contracts between the virtual clinic and other entities.

Referring now to FIG. 2, the method of the present invention starts out generally at step 202. Initially, a virtual clinic is established, step 204, and this generally may be any known virtual clinic such as a corporation or partnership. The virtual clinic establishes a working relationship, often in the form of a contract or other obligation, with physicians, step 206, to provide medical services to one or more patients. The virtual clinic establishes contracts with insurance companies, step 208, to, for example, reimburse the virtual clinic for medical services provided to the patients. The virtual clinic may establish contracts with one or more hospitals, step 210, to provide diagnostic testing or medical services which require the patient's presence. The hospital of step 210 can be a standard hospital, however, it is envisioned to encompass not only hospitals but may also include a standard clinic, a laboratory, or other diagnostic/treatment facilities that provide technical services and/or equipment not found in the patient's home. The virtual clinic also establishes contracts with patients, step 212, such that the patient will provide payment in return for receiving medical services. Here, the payment may be authorization of the insurance company to pay all or part of the fee for the medical services or the patients may directly pay the fee for the medical service and possibly request reimbursement from the insurance company.

Figure 3:
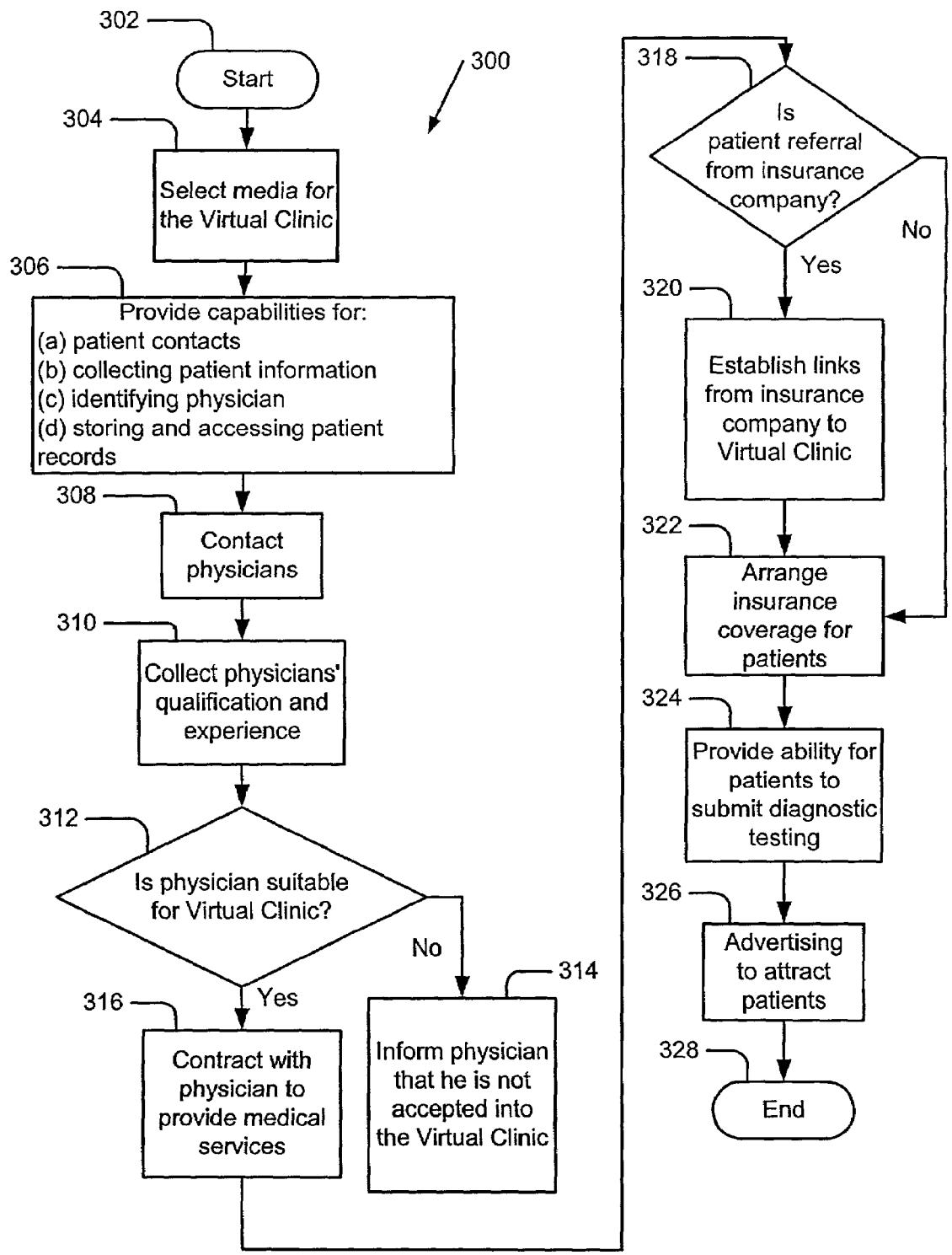
FIG. 3 is a flow chart of an embodiment of the present invention showing the development of a virtual clinic for allowing a patient remotely contacting a physician and receiving medical services.

Referring to FIG. 3, the flow chart 300 shows an embodiment of the present invention showing the development of a virtual clinic. The method starts out generally at step 302. First, a media is selected for the virtual clinic, step 304. Preferably, the media is the Internet and the virtual clinic is represented on an Internet site and has Internet connections to, for example, physicians, insurance companies, a hospital, clinic, laboratory, or other diagnostic facility, and allows patients to access the Internet site directly or may allow insurance companies to electronically tie to the virtual clinic's site. The media may also be a phone system, for example, an automated phone system.

Preferably, the virtual clinic has a combination of hardware and software which provides capabilities for:

(a) patient contacts;
(b) collecting patient information;
(c) identifying physician based on patient's submitted information on his or her medical condition; and
(d) storing and accessing patient records, step 306.

The virtual clinic contacts physicians, step 308, and collects qualifications and experience, step 310. Preferably, the virtual clinic determines whether the physician is suitable for providing medical services for patients referred by the virtual clinic, step 312, and if not, the physicians are informed that they are not accepted into the virtual clinic, step 314. If the physicians are suitable for the virtual clinic, a contract, partnership, or other working relationship is entered into between the physician and the virtual clinic, providing that the physician will provide medical services to patients referred to it by the virtual clinic, step 316. In addition to contracting with physicians, the virtual clinic may also contract or partner with other organizations, such as hospitals, clinics (both inpatient and outpatient), laboratories, and other diagnostic/treatment facilities.

As noted above, patients may be referred to the virtual clinic from a number of sources, including referrals from insurance companies. Preferably, the virtual clinic determines if the patient referral is from an insurance company, step 318, and if so, an attempt is made to establish links from the insurance company to the virtual clinic, step 320. If not, preferably, steps are taken to arrange insurance coverage for the patient, step 312.

Hardware, software, and equipment is preferably provided to provide the ability for patients to submit diagnostic test results to physicians, step 324. Preferably, the virtual clinic advertises to attract patients, step 326. The advertising may be directed at individual patients or may be directed at insurance companies to refer patients to the virtual clinic, for example, by providing lower cost medical services for the insurance company's benefit.

The preferred equipment for use in conjunction with the preferred virtual clinic may consist of:

1. A personal computer;
2. Access to the Internet;
3. Digital video camera or computer camera in operative communication with the computer;
4. Weighing machine;
5. Thermometer;
6. Electronic pulse, blood pressure, pulse oximeter, stethoscope, home blood sugar monitoring apparatus, if appropriate;
7. Digital scope for viewing mouth and external ears;
8. EKG machine, if appropriate;
9. Compact portable ultrasound equipment, if desired; and
10. Any other equipment as may become available in the future within the financial reach of the average family.

In addition, some families may have other equipment at the home if they have a family member with a chronic condition. For example, patients with diabetes may have additional equipment in the home for testing blood sugar levels that would not be found in the average home. For purposes of this disclosure, it is envisioned that any of the additional equipment for these chronic conditions, whatever they are, may be equipped to communicate on the same or other channels available to the patient and can be utilized by the patient, the physician, and the virtual clinic to provide additional diagnostic information.

Most of these, except items no. 9 and 10, are available and relatively inexpensive. Item no. 6 is typically purchased as a single pack, and several of these instruments could be packaged into a single device (see U.S. Pat. No. 5,701,904) which can be directly connected to an inlet port in the PC. Preferably, the virtual clinic provides a way for the physician to determine what diagnostic testing equipment is available to the patient, either at the patient's home or at a conveniently located public facility. While the patient should know what diagnostic testing equipment exists at his residence, and can enter this information upon being prompted, he may not appreciate what equipment exists at nearly public facilities. In this case, the virtual clinic may keep track of the diagnostic testing equipment located at public facilities, and use, for example, zip codes to determine if the public facility is near the patient.

Figure 4:
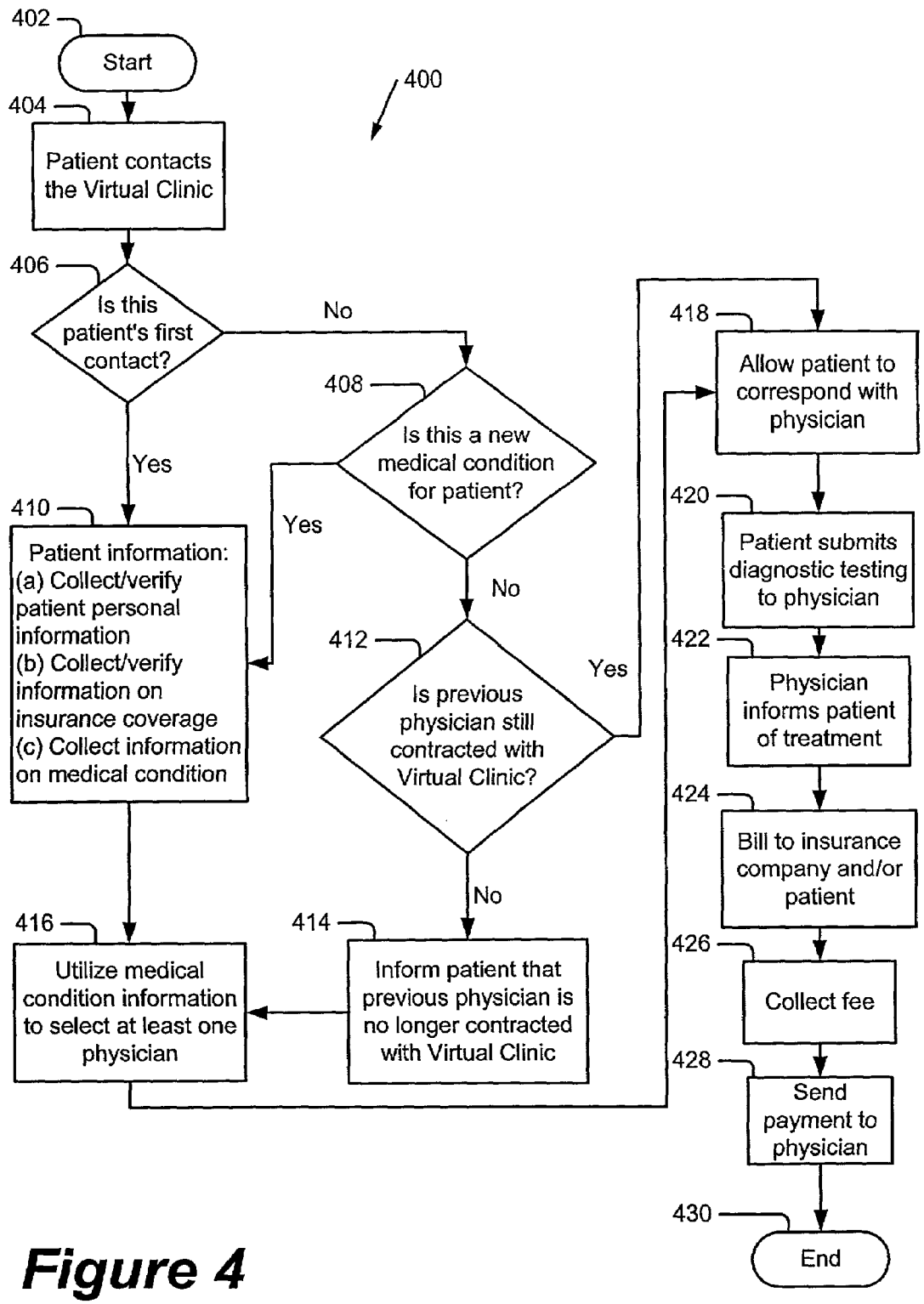
FIG. 4 is a flow chart of an embodiment of the present invention showing a method for a patient remotely contacting a physician and receiving medical services.

FIG. 4 shows a flow chart 400 of an embodiment of the present invention. The method starts out generally at step 402. The patient contacts the virtual clinic, step 404, and this may be through a direct contact or may be a referral through an insurance company. Preferably, a questionnaire is provided which asks whether this is the patient's first contact with the virtual clinic, step 406. If it's not the patient's first contact, then the patient is questioned about whether he has a new medical condition, step 408. If either it is the patient's first contact, step 406, or the patient has a new medical condition, step 408, then the patient provides additional information such as:

(a) collect/verify (if existing patient) patient personal information;
(b) collect/verify information on insurance coverage; and
(c) collect information on medical condition. Step 410.

If the patient is an existing client, step 406, and is receiving continuing treatment for a medical condition, step 408, then, preferably, a determination is made whether the previous physician is still contracted with the virtual clinic, step 412. If not, the patient is informed that his previous physician is no longer connected with the virtual clinic, step 414, and the patient's information regarding his medical condition is used to select at least one other physician to provide the patient with medical services, step 416. If the patient's previous physician is still connected with the virtual clinic, step 412, or the patient receives a new physician pursuant to step 416, then the patient is allowed to correspond with the physician, step 418, and submit diagnostic testing to the physician, step 420, such that the physician may inform the patient of treatment, step 422.

The virtual clinic submits a bill to the insurance company and/or the patient, step 424, and the virtual clinic collects the fee for the medical services from the insurance company and/or patient, step 426, and a portion of this fee is sent to the physician, step 428.

Figure 5:
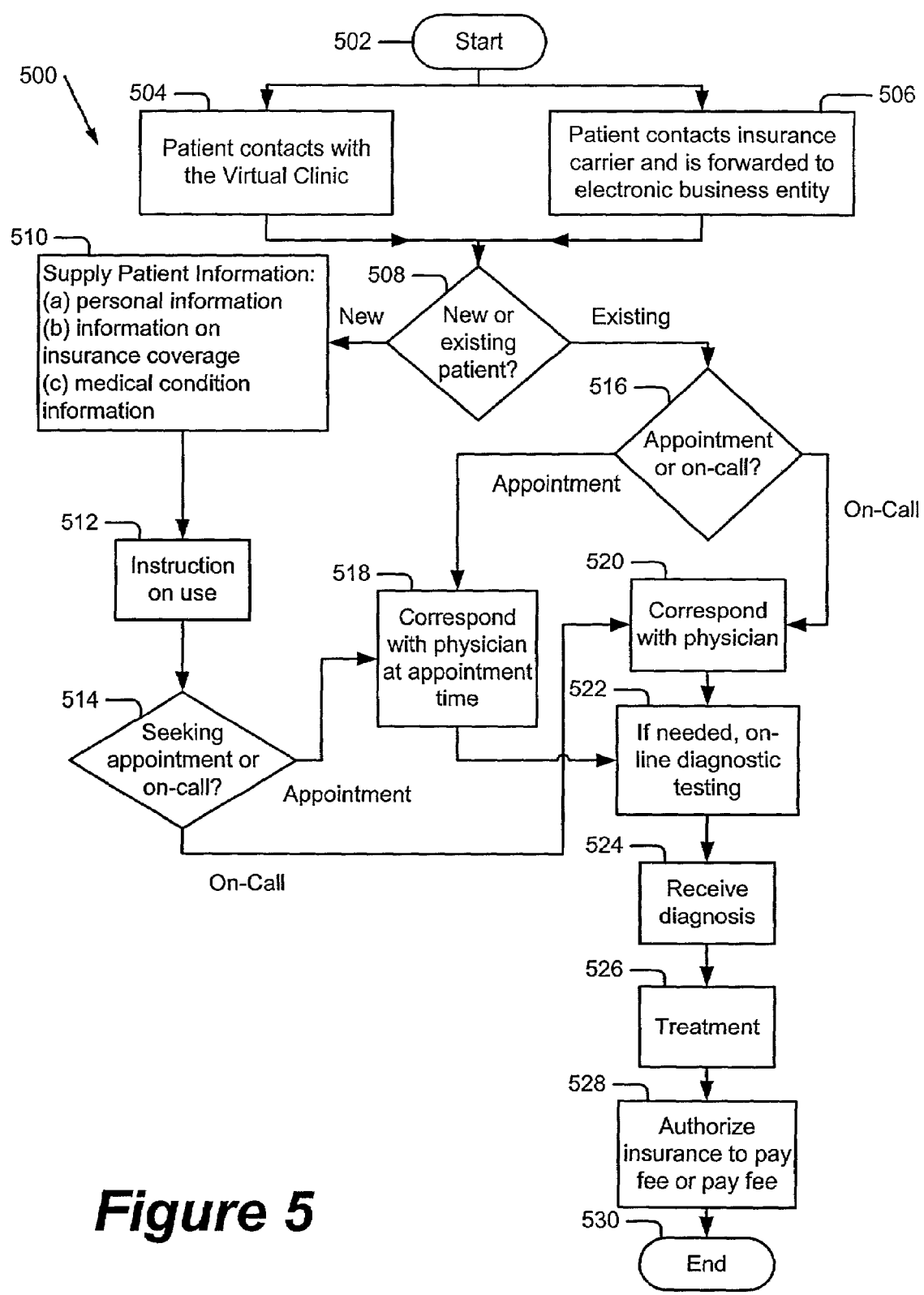
FIG. 5 is a flow chart of an embodiment of the method of the present invention from a patient's perspective.

FIG. 5 is a flow chart 500 of an embodiment of the method of the present invention from a patient's perspective. The method starts out generally at step 502. The patient may contact the virtual clinic directly, step 504, or the patient may contact an insurance carrier and be forwarded or otherwise referred to the virtual clinic, step 506. Alternatively, the patient may approach the virtual clinic after being directed to do so by word-of-mouth advice from friends or family for which the virtual clinic may receive a finder fee or partial payment from the physician. Additionally, the virtual clinic may attract patients directly through advertisement, preferably on the Internet, by placing adds with insurance carriers, laboratories, household equipment manufacturers, employer, famous web portals, and web sites that cater to people seeking medical advice or medical attention for which the virtual clinic can pay the site owners for the "click-through." The way in which the patient learned of the virtual clinic can be optionally verified when the patient is questioned regarding whether he/she is a new or existing patient, step 508, and if a new patient, then the patient is asked to supply patient information, including:

(a) personal information;
(b) information on insurance coverage; and
(c) medical condition information, step 510.

If the patient is new to the virtual clinic (under step 508), then the patient is provided instructions on the use of the system, step 512, and is questioned regarding whether he/she is seeking an appointment or wishing to converse with a physician on-call, step 514.

Referring back to step 508, likewise, if the patient is an existing patient, he is questioned whether he seeks an appointment or an on-call contact with a physician. From step 514 and step 516, if a patient wishes to correspond with physician pursuant to an appointment, an appointment is set up through the virtual clinic with both the patient and physician, such that the patient may correspond with the physician at the appointment time, step 518. If from step 514 or step 516 the patient wishes to converse with a physician on-call, then the patient's information on his/her medical condition is used to determine a suitable physician and the virtual clinic determines whether that physician is on-call at that time. If the physician is on-call, the patient may correspond directly with the physician, step 520. If needed, the physician and patient may conduct on-line diagnostic testing, step 522, then, the patient receives a diagnosis, step 524, and the physician recommends a treatment, step 526. Next, arrangements are made for the patient to authorize the insurance company to pay the fee for the medical service or for the patient to pay the fee directly, step 528.

Figure 6:
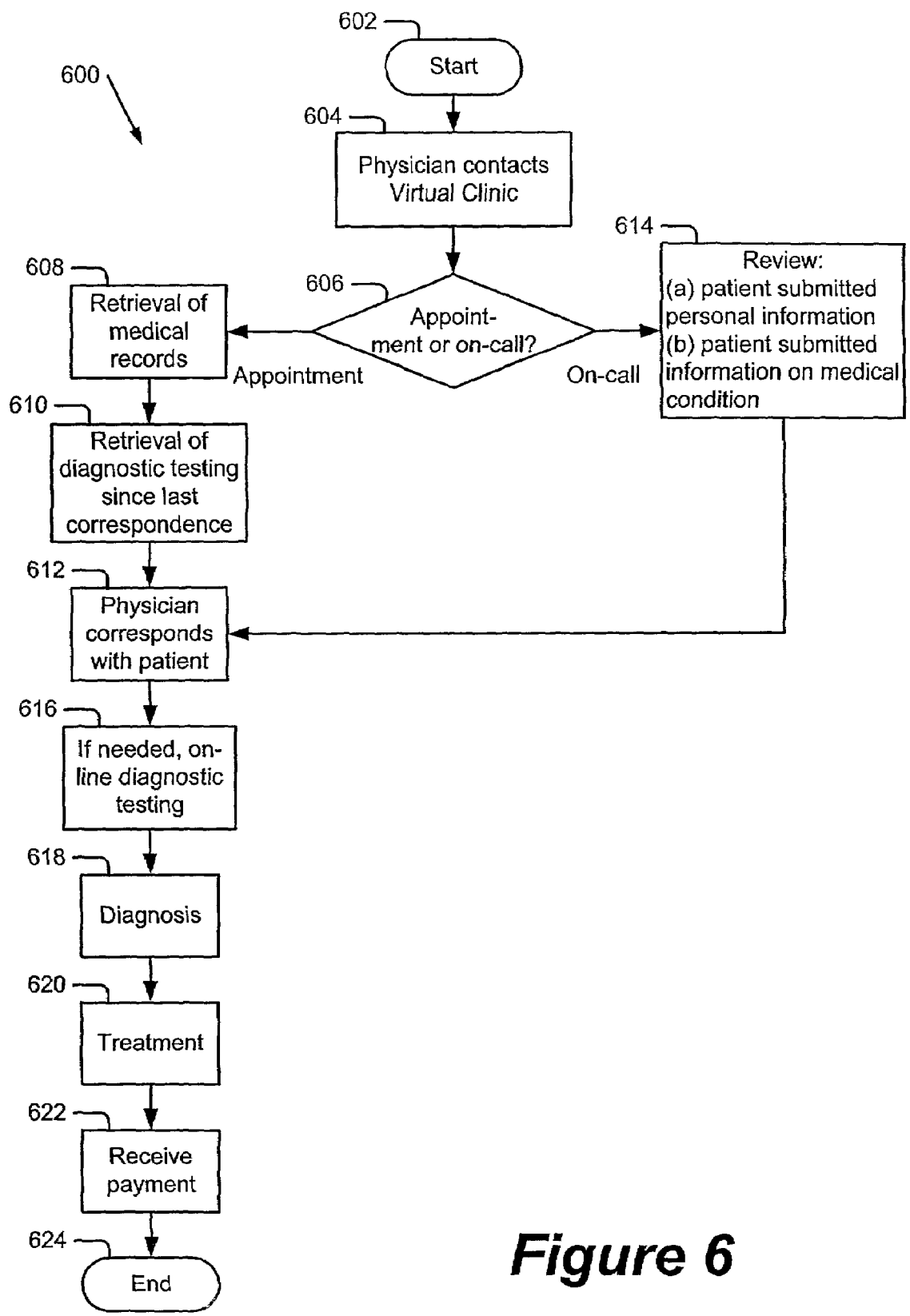
FIG. 6 is a flow chart of an embodiment of the method of the present invention from a physician's perspective.

FIG. 6 shows a flow chart 600 of an embodiment of a method of the present invention from a physician's perspective. The method starts out generally at step 602. Initially, the physician contacts the virtual clinic, step 604, informing the virtual clinic whether he is going on-line to conduct an appointment or is available for on-call conferences, step 606. If the physician is conducting an appointment, he may first retrieve the patient's medical records, step 608, and retrieve any diagnostic testing since his last correspondence with the patient, step 610, and then correspond directly with the patient, step 612. If the physician is on-call (from step 606), before corresponding with a patient, step 612, he may first review the patient-submitted personal information and the patient-submitted information on his/her medical condition, step 614, such that the physician may more thoroughly address the patient's concerns. If needed, on-line diagnostic testing may be conducted, step 616, a diagnosis is made by the physician, step 618, the physician recommends treatment, step 622, and, after the virtual clinic receives its payment, it forwards a payment on to the physician, step 624.

An embodiment of this invention includes a virtual clinic comprising an electronic network system providing services between professionals and clients. A preferred embodiment includes such a virtual clinic for providing medical services. Another embodiment includes on-site monitoring and testing in conjunction with the virtual clinic. Yet another embodiment includes associated services such as insurance coordination and appointments in conjunction with the virtual clinic.

A preferred embodiment is an Internet-based system. The virtual clinic could operate nationally and could have a physician in California treat a patient in New York as long as the physician has a New York state license. The advantage would be that the physician could be working at 4:00 p.m. California time (regular work time) while the patient would be at home at 7:00 p.m., New York time, a difficult, if not impossible time to find a physician for a regular follow up visit to review a change in medicine for diabetes.

The patient and physician are able to see each other via a camera hooked up to their PCs and can communicate directly with each other verbally or by typing on their respective screens.

When the patient is placed in contact with his or her doctor, the doctor may have a prepared screening questionnaire on the Internet which the patient completes, providing details of the nature of the problem, relevant past and family medical history, medications the patient is taking, any known drug allergies, etc. The doctor may choose to have a separate consent for treatment and payment form signed electronically by the patient.

The physician or his/her nurse, PA, etc., would review the questionnaire completed by the patient and ask any additional relevant questions. The physician would then direct the patient to weigh, to record his/her temperature, and to place his/her finger in the digital blood pressure/pulse recording device (vital signs recording). The physician can view the patient and see if he/she is in pain, short of breath or otherwise uncomfortable, or appears anxious, depressed, etc. The physician or physician's assistant could ask the patient to place the digital electronic scope to view the oral cavity (mouth) and inside the ear canal. The physician or physician's assistant would then require the patient to place the electronic stethoscope over different points of his/her body (heart, lungs, abdomen) directing the patient to breathe or hold his/her breath as appropriate (perform telecommunication). A family member or friend at home or at a place of work could easily assist with placement of the stethoscope in different positions as directed by the physician (perform tele-examination). The virtual clinic would provide audio/video instructions for above both on the Internet and by mail to the patients.

The virtual clinic could provide slightly more elaborate, but still relatively inexpensive set-ups with EKG, spirometry and compact portable digital ultrasound devices in places of work or any other remote location (where it would be cost effective for the employer rather than have loss of worker's time visiting a doctor). Additionally, employers, apartment complexes, homeowners' associations, etc. may set up a designated room suitably equipped for use with the virtual clinic that is accessible to members who do not have a PC at home. Patients themselves can add extra diagnostic equipment to their homes that supplement the diagnostic phase, particularly for patients with chronic conditions where the expense of the extra equipment can be readily justified.

The physician, with the data obtained, could order appropriate medication which could be called or faxed or e-mailed to a pharmacy. The virtual clinic may provide an electronic pharmacy service offering the best price on the medicine prescribed for the patient if the patient chooses, or the virtual clinic may maintain a licensed pharmacy to dispense medicines to the patient.

The physician may order laboratory or radiological imaging investigations via the virtual clinic. An order for the tests could be electronically communicated directly to the appropriate facility. The patient could set up a mutually convenient time with the facility to have the tests run. The laboratory or imaging facility will electronically communicate the results to the physician and electronically load imaging films taken on digital format for physicians to review and share with the patient, as necessary. The physician could set up a follow up visit with the patient through the virtual clinic to explain the results of tests, advise appropriate corrective measures, medications, if necessary, and provide educational material to the patient on the wide area network (e.g., aerobic exercise for reduction of lipids (fats) in the blood or specific exercises for back strain). The physician could have educational material available electronically or direct the patient to a web site from which the patient can print them on his/her printer.

The physician may require the patient to come into the office in person for a more detailed examination or refer the patient to a specialist.

Several other examinations can be performed on the patient including, but not limited to, the evaluation of the following: skin abnormalities through digital video camera, patient's gait by requesting patient to walk, swelling of joints, movement or restriction of joints, and tender spots by asking the patient to press on different parts of the body and reporting any tenderness, weakness in either side of the body by asking the patient to lift weights, coordination by viewing patient's handwriting, etc.

More sophisticated tests, such as visual field examination for screening for glaucoma can be done (see U.S. Pat. No. 6,033,076). A diabetic patient may monitor blood sugar at home and enter the data either through the virtual clinic's web site or physician e-mail which the physician may access at his/her convenience and inform the patient electronically of any adjustment in doses or medicine, change in diet, or activity recommendations, etc. The virtual clinic can also be equipped with circuitry and/or software that can monitor and/or compare the results of diagnostic tests that the patient (or a laboratory, etc.) uploads to the virtual clinic and, if necessary, analyze the uploaded data by, for example, comparing the test results to pre-determined limits set by the physician and/or against pre-set values or the patient's past values that can be stored in a database that is accessible to the virtual clinic. If the new test values falls below a minimum value, or exceeds a maximum threshold, the virtual clinic can issue a signal to the patient's physician or to an on-call physician or other medical service provider to prompt follow-up care for the patient. The virtual clinic can be equipped with circuitry and/or software that stores the pre-set limits by the physician or by generally accepted levels set by another organization (such as the American Medical Association). For example, referring to FIG. 1, the patient 104, the diagnostic test equipment 122, and/or the hospital/clinic/laboratory 118 could upload diagnostic information (temperature, blood test results, etc.) to the virtual clinic 102 by the communication channels 106, 126, 128, respectively. The virtual clinic 102 could be provided with a database internally, or it could access another database at, for example, the insurance company 112 or the hospital/clinic/laboratory 118. The uploaded data is then compared to the pre-set values (either pre-selected by the physician, an organization, and/or the patient's previously determined values) and, if the difference between the pre-set values and the uploaded values is higher or lower than a pre-determined threshold, a signal can be issued by the virtual clinic 102 to the physician 108 via communication channel 110. Incidentally, the physician 108 need not be the patient's personal physician, it can be an on-call physician (optionally determined by the virtual clinic) or other medical service provider such as a physician's assistant, nurse, nurse practitioner, technician, social worker, etc.

With the virtual clinic, doctors do not have to maintain traditional office hours, as they could evaluate patients electronically from home, vacation spots, or at non-traditional hours or days of the week. Similarly, patients do not have to maintain traditional hours for routine office visits. If the diagnostic equipment is carried by the patient (such as a heart monitor), the recorded or real-time information can be uploaded automatically to the virtual clinic for analysis and forwarding of results (either normally or as part of an alert message) to the physician 108.

The doctor may be in a different time zone as long as he has a license to practice in the state where the patient is located, thus making it convenient for patients to visit doctors late in the evening, for example, a doctor in California at 4 p.m. Pacific time could consult with a patient located in New York at home at 7 p.m. Eastern time. They could, in fact, be in different countries as long as they are appropriately licensed. This would also expand the scope of practice for U.S. physicians who could advise and consult with patients outside the U.S. where the availability of medical services, especially experts, is severely limited or co-consult with an expert outside of the U.S.

Another advantage of the system is, if a patient cancels or does not log-on for appointment, the next one can be serviced immediately, electronically (as opposed to another patient driving to the doctor's office, which is not practical, given the time constraints). There would be no weather-related cancellations. Additionally, if the doctor is delayed, the patient may attend to other things at home or work.

The physician's assistant (PA, nurse, etc.) could perform a physical exam and store the data in an electronic format for the physician to review later, and the practitioner then advises the physician. Additionally, the physician's assistant could follow a preset protocol, such as obtaining certain diagnostic tests if the patient's temperature is greater than 101 degrees Fahrenheit.

The virtual clinic would maintain medical records and forward them, at the patient's direction, to any physician or consultant whom the patient identifies. As these records would be electronically stored and accessible, there would be a seamless transfer of data to another physician or consultant, if needed. If a patient sees a different physician at different times or needs to see multiple consultants, all of them would have access to the information simultaneously (much better than the present systems of carrying copies of charts) or would be able to interact with or without the patient simultaneously. Of course, security and confidentiality would have to be considered and incorporated into the system and all legal requirements satisfied. The physician could maintain a copy of all records and data for his/her personal files. A patient could also maintain his/her records in a CD format.

The virtual clinic is intended to operate as a for-profit virtual clinic. There are several ways in which the virtual clinic can make profits. Preferably, the virtual clinic receives payment directly from the insurance company or patient and then retains a percentage and forwards the remainder on to the physicians. Of course, the virtual clinic's retained percentage must cover its cost, such as maintaining an Internet-based system and, possibly, purchasing and maintaining diagnostic testing equipment located in publicly accessible areas and used for groups. Also, the virtual clinic could promote paid advertising for health and medical related products and services.

In an alternate embodiment, the physician may provide all of these services on the net without the intervention of an e-virtual clinic and charge appropriately for the services he/she provides. In this set up, the patient would access a physician's web site through which the physician or his/her assistant can guide the patient to the appropriate questionnaires and evaluation by the physician at a mutually convenient time after proper consents for treatment and payment have been completed.

The invention, therefore, is well adapted to carry out the objects and attain the ends and advantages mentioned, as well as others inherent therein. While the invention has been depicted, described, and is defined by reference to exemplary embodiments of the invention, such references do not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A method, comprising:
    establishing a virtual clinic on a network;
    the virtual clinic having working relationships with medical professionals;
    the virtual clinic having working relationships with patients;
    the virtual clinic being associated with diagnostic centers, each diagnostic center having diagnostic testing equipment for generating diagnostic test results, a particular diagnostic center being other than a treatment-providing facility or a patient's private home;
    the virtual clinic storing, for each diagnostic center, the location of the diagnostic center and identification of at least a portion of the diagnostic testing equipment at the diagnostic center;
    receiving a request for medical services from the particular patient by the virtual clinic;
    establishing a real-time electronic communications link between the particular patient and a particular medical professional by the virtual clinic;
    receiving a request for a diagnostic test by the particular patient from the particular medical professional;
    enabling the particular patient to obtain the location of at least one diagnostic center having diagnostic test equipment corresponding to the diagnostic test, the at least one diagnostic center including the particular diagnostic center;
    obtaining particular diagnostic test results by the particular patient at the particular diagnostic center, the diagnostic test being administered by a non-medical-professional; and
    communicating the particular diagnostic test results electronically to the particular medical professional.

2. The method of claim 1, further comprising:
    accessing a web page by the patient that is provided by the virtual clinic;
    receiving, by the virtual clinic, information about the patient; and
    based upon the information about the patient, selecting a medical professional.

3. A method for delivering patient care, comprising:
    establishing a virtual clinic on a network;
    the virtual clinic having a working relationship with an insurance carrier, the insurance carrier having a patient to which the insurance carrier provides benefits;
    the virtual clinic having a working relationship with one or more medical professionals;
    the virtual clinic being associated with diagnostic centers, a particular diagnostic center being other than a treatment-providing facility or a patient's private home, each diagnostic center having diagnostic testing equipment;
    the virtual clinic storing, for each diagnostic center, the location of the diagnostic center and identification of at least a portion of the diagnostic testing equipment at the diagnostic center;
    receiving a request for medical services from the patient;
    establishing a real-time electronic communications link between the patient and a particular medical professional of the one or more medical professionals by the virtual clinic;
    receiving a request for a diagnostic test by the patient from the particular medical professional;
    enabling the patient to obtain the location of at least one diagnostic center having diagnostic testing equipment corresponding to the diagnostic test, the at least one diagnostic center including the particular diagnostic center;

obtaining particular diagnostic test results by the patient at the particular diagnostic center, the diagnostic test being administered by a non-medical-professional; and communicating the particular test results electronically to the particular medical professional.

4. The method of claim 3, further comprising:

accessing a web page by the patient that is provided by the insurance carrier;

receiving, by the insurance carrier, information from the patient through the web page;

forwarding the information to the virtual clinic;

based upon the information, selecting a medical professional.

5. A system comprising:

a network;

a medical professional device for use by a medical professional and enabled to receive information from the network and to submit responses on the network;

a patient device for use by a patient and enabled to submit information on the network and to receive responses from the network;

diagnostic centers, each having diagnostic testing equipment, a particular diagnostic center being other than a treatment-providing facility or the patient's private home, the particular diagnostic center having diagnostic testing equipment being administered by a non-medical-professional; and a virtual clinic associated with the diagnostic centers, the virtual clinic storing the location of each diagnostic center and identification of at least a portion of the diagnostic testing equipment at each diagnostic center, the virtual clinic being configured to receive information and responses from the network, to select the medical professional based upon the information provided by the patient, to enable real-time electronic communication of the information and the responses between the medical professional device and the patient device, to enable the patient to obtain the location of at least one diagnostic center having diagnostic testing equipment corresponding to a diagnostic test requested by the medical professional, the at least one diagnostic center including the particular diagnostic center, and to enable electronic communication of particular diagnostic test results from the particular diagnostic center to the medical professional device.

6. The system as in claim 5, the system further comprising:

a hospital enabled to receive the information from the network and to submit responses.

7. A system comprising:

a network;

a medical professional device for use by a medical professional and enabled to receive information from the network and to submit responses on the network;

a patient device for use by a patient and enabled to make a request for medical services, to submit the information on the network and to receive the responses from the network;

diagnostic centers, each having diagnostic testing equipment, a particular diagnostic center being other than a treatment-providing facility or the patient's private home, the particular diagnostic center having diagnostic testing equipment being administered by a non-medical-professional;

an insurance carrier being configured to receive the request for medical services from the patient and to forward the request to a virtual clinic, the virtual clinic being associated with the diagnostic centers and storing the location of each diagnostic center and identification of at least a portion of the diagnostic testing equipment at each diagnostic center, the virtual clinic being configured to receive the information and the responses from the network, the virtual clinic being configured to select the medical professional based upon the information provided by the patient, the virtual clinic being configured to enable real-time electronic communication of the information and the responses between the medical professional device and the patient device, the virtual clinic being capable of enabling the patient to obtain the location of at least one diagnostic center having diagnostic test equipment corresponding to a diagnostic testing requested by the medical professional, the at least one diagnostic center including the particular diagnostic center, and the virtual clinic being capable of enabling electronic communication of particular diagnostic test results from the particular diagnostic center to the medical professional device.

8. The system as in claim 7, the system further comprising:

a hospital enabled to receive the information from the network and to submit responses.

9. A method, comprising:

establishing a virtual clinic including an electronic portal to medical care, the virtual clinic having capabilities for:
 (a) enabling a patient to contact the virtual clinic,
 (b) collecting information on the patient's medical condition,
 (c) identifying at least one medical professional based on the collected information, and
 (d) accessing the patient's medical records;

establishing a working relationship with the least one medical professional to provide medical services to patients referred via the virtual clinic, the medical professional providing information relating to qualifications for use during a selection process;

providing diagnostic testing equipment at diagnostic centers associated with the virtual clinic, a particular diagnostic center being other than a treatment-providing facility or the patient's private home, the particular diagnostic center having diagnostic testing equipment being administered by a non-medical-professional; and enabling by the virtual clinic real-time electronic communication among a patient device operated by the patient, a medical professional device operated by the medical professional, and the particular diagnostic center to transmit the information regarding the patient's condition to the medical professional device, diagnostic test requests by the medical professional to the patient device, results from the particular diagnostic center to the medical professional device, and recommended treatment to the patient device; and enabling the virtual clinic to inform the patient of the location of at least one diagnostic center having diagnostic testing equipment corresponding to a diagnostic test requested by the medical professional, the at least one diagnostic center including the particular diagnostic center.

10. The method of claim 9 further comprising:

submitting information relating to medical licenses by the medical professional; and comparing a patient's residence with the medical professional's medical license by the virtual clinic.

11. The method of claim 9 further comprising:
providing the patient with access to the diagnostic testing equipment.

12. The method of claim 9, wherein the virtual clinic has a presence on at least one Internet site.

13. The method of claim 9, wherein the virtual clinic further has the capability for at least one insurance company to refer patients to the virtual clinic.

14. The method of claim 9, wherein the virtual clinic has the capability for at least one hospital to refer patients to the virtual clinic.

15. The method of claim 9, wherein the virtual clinic has the capability for informing a medical professional of diagnostic testing equipment results.

16. The method of claim 9, wherein the virtual clinic has the capability for allowing a medical professional to access and update a patient's medical records.

17. The method of claim 9, further comprising:
contracting with at least one hospital to provide access to diagnostic testing equipment to patients of the virtual clinic.

18. A method, comprising:
a patient contacting a virtual clinic;
the patient providing information on his medical condition to the virtual clinic;
the virtual clinic identifying a medical professional based on the patient-provided medical condition information;
the virtual clinic enabling real-time electronic communication between a patient device operated by the patient and a medical professional device operated by the identified medical professional;
the patient corresponding electronically with the medical professional;
the medical professional requesting the patient to take a diagnostic test;
the virtual clinic informing the patient of the location of at least one diagnostic center associated with the virtual clinic and having diagnostic testing equipment corresponding to the diagnostic test;
the virtual clinic enabling the patient to access a particular diagnostic center being other than a treatment-providing facility or the patient's private home, the diagnostic center having diagnostic testing equipment corresponding to the diagnostic test;
the particular diagnostic test equipment being administered by a on-medical-professional and electronically providing the diagnostic test results to the medical professional; and
the medical professional informing the patient of recommended treatment.

19. The method of claim 18, further comprising:
at least one insurance company referring at least one patient to the virtual clinic.

20. The method of claim 18, further comprising:
at least one hospital referring at least one patient to the virtual clinic.

21. The method of claim 18, further comprising:
the virtual clinic receiving payment for medical services provided.

22. The method of claim 21, further comprising:
the virtual clinic forwarding a portion of the received payment to the medical professional.

23. The method of claim 18, further comprising:
informing the medical professional of the diagnostic testing equipment available to the patient.

24. The method of claim 18, further comprising:
at least one medical professional providing information relating to medical licenses and the virtual clinic comparing a patient's residence with a medical professional's medical license.

25. The method of claim 18, wherein the step of identifying a medical professional based on the patient-provided medical condition information comprises medical professionals providing information relating to qualifications and the virtual clinic comparing the patient-provided medical condition information with the medical-professional-provided information relating to qualifications.

26. The method of claim 18, further comprising:
the patient contracting with the virtual clinic to provide payment in return for receiving medical services.

27. The method of claim 18, further comprising:
at least one insurance company reimbursing the virtual clinic for medical services provided to at least one patient.

28. The method of claim 18, further comprising:
at least one physician reimbursing the virtual clinic for directing the patient to the medical professional.

29. A virtual clinic, comprising:
a web page for enabling a patient to request consultation with a medical professional and to provide medical condition information;
a medical professional database for storing contact information and qualifications for a set of medical professionals;
a medical professional selection component for selecting one of the medical professionals in the medical professional database based on predetermined criteria;
a communication component for enabling real-time electronic communication between the selected medical professional and the patient;
memory for storing the location of each of a plurality of diagnostic centers associated with the virtual clinic and identification of diagnostic test equipment at each of the plurality of diagnostic centers, a particular diagnostic center being other than a treatment-providing facility or the patient's private home;
a communication component for informing the patient of at least one diagnostic center having diagnostic test equipment corresponding to a diagnostic test requested by the selected medical professional, the at least one diagnostic center including the particular diagnostic center; and
a diagnostic test equipment communication component for electronically communicating with particular diagnostic test equipment at the particular diagnostic center to obtain diagnostic test results of a patient taking the diagnostic test requested by the selected medical professional, the diagnostic test being administered by a non-medical professional.

30. The virtual clinic of claim 29, wherein the predetermined criteria involves one of the qualifications of the medical professional, the patient's medical condition information, the time of the request, scheduling information, location of the patient, patient request, patient preferences, availability of a patient's standard physician, insurance information, employer information, and a prior medical professional assisting the patient.

31. The virtual clinic of claim 29, further comprising a patient records accessing component for communicating with a patient records database to provide patient records information to the medical professional.

32. The method of claim 1, wherein the particular diagnostic center is located in an apartment complex.

33. The method of claim 1, wherein the particular diagnostic center is located in a workplace of the particular patient.

34. The method of claim 1, wherein the particular diagnostic center is located in a public facility.

35. The system of claim 5, wherein the particular diagnostic center is located in an apartment complex.

36. The system of claim 5, wherein the particular diagnostic center is located in a workplace of the patient.

37. The system of claim 5, wherein the particular diagnostic center is located in a public facility.

38. The clinic of claim 29, wherein the location is an apartment complex.

39. The clinic of claim 29, wherein the location is a workplace of the patient.

40. The clinic of claim 29, wherein the location is a public facility.

* * * * *

UNITED STATES PATENT AND TRADEMARK OFFICE
CERTIFICATE OF CORRECTION

| | |
|---|---|
| PATENT NO. | : 7,412,396 B1 |
| APPLICATION NO. | : 09/918413 |
| DATED | : August 12, 2008 |
| INVENTOR(S) | : Mohamed M. Haq |

It is certified that error appears in the above-identified patent and that said Letters Patent is hereby corrected as shown below:

Column 17, line 47, "on-medical-professional" should be changed to --non-medical-professional--.

Signed and Sealed this

Thirtieth Day of June, 2009

JOHN DOLL
*Acting Director of the United States Patent and Trademark Office*